United States Patent [19]

Brewer et al.

[11] Patent Number: 4,728,613

[45] Date of Patent: Mar. 1, 1988

[54] METHOD FOR THE RECOVERY OF EXTRACELLULAR ENZYMES FROM WHOLE FERMENTATION BEER

[75] Inventors: Jack W. Brewer, Elkhart, Ind.; Charles E. Brothers, Cassopolis, Mich.; Terry F. Farver; Chong Y. Kim, both of Elkhart, Ind.; Eunkyu Lee, Granger, Ind.

[73] Assignee: Miles Laboratories, Inc., Elkhart, Ind.

[21] Appl. No.: 890,620

[22] Filed: Aug. 5, 1986

Related U.S. Application Data

[63] Continuation-in-part of Ser. No. 775,031, Sep. 4, 1985, abandoned.

[51] Int. Cl.[4] .......................... C12N 9/56; C12N 9/00; C12N 9/28
[52] U.S. Cl. ..................................... 435/222; 435/183; 435/202; 435/814; 435/816
[58] Field of Search ........ 435/183, 201, 202, 219–222, 435/814, 816

[56] References Cited

U.S. PATENT DOCUMENTS

| | | | |
|---|---|---|---|
| 3,415,804 | 12/1968 | Poison | 435/199 X |
| 3,819,528 | 6/1974 | Berry | 435/188 X |
| 4,144,130 | 3/1979 | Kula et al. | 435/183 |
| 4,508,825 | 4/1985 | Kim et al. | 435/201 |
| 4,591,563 | 5/1986 | Paul et al. | 435/193 |

OTHER PUBLICATIONS

"Protein Recovery Using Two-Phase Systems", Hustedt et al., *Trends in Biotechnology*, vol. 3, No. 6, pp. 139–144, 1985.

*Primary Examiner*—Lionel M. Shapiro
*Attorney, Agent, or Firm*—Louis E. Davidson

[57] ABSTRACT

Extracellular enzymes can be recovered from a whole fermentation beer by adding to the whole beer a mixture of a polymer and an inorganic salt. This total mixture produces an enzyme-rich polymer phase and a cell debris-containing, enzyme-poor salt phase which can be separated to produce an enzyme-rich product from the polymer phase.

16 Claims, No Drawings

METHOD FOR THE RECOVERY OF EXTRACELLULAR ENZYMES FROM WHOLE FERMENTATION BEER

This is a continuation-in-part of U.S. patent application Ser. No. 775,031, filed on Sept. 4, 1985 now abandoned.

BACKGROUND OF THE INVENTION AND PRIOR ART

The production of industrial enzymes by culturing microorganisms, such as bacteria, fungi and yeast, in aqueous nutrient media is well-known. Depending on the nature of the particular microorganism, the enzyme(s) produced may be extracellular, intracellular, or a mixture thereof. When the enzyme(s) produced are extracellular, they are generally obtained by first separating the enzyme-containing supernatant from the microorganism cells and then recovering the enzyme(s) from the supernatant by well-known methods, such as precipitation, ultrafiltration and evaporation. When the enzyme(s) produced are intracellular, they must first be released from the cells. This can be accomplished chemically and/or mechanically. Once the enzyme(s) are placed into a solution, they can also be recovered by the above well-known methods.

It is known that extracellular enzymes have compositions and properties which are different from intracellular enzymes. Extracellular enzymes, for example, generally have significantly lower molecular weights than intracellular enzymes. The solution containing intracellular enzymes released from the cells will also contain significant quantities of other intracellular material that are not present in a whole fermentation beer containing extracellular enzymes. These differences can cause different procedures to be employed for recovery and purification thereof even when they are both in aqueous solution. A recovery procedure suitable for intracellular enzymes is thus not obviously useful for extracellular enzymes.

In order to improve the efficiency and convenience of enzyme production and recovery, it is known that enzymes can be produced by a microorganism fermentation in a two-phase nutrient medium containing a mixture of polyethylene glycol and dextran. At the completion of the fermentation, the extracellular enzyme is concentrated in the upper polyethylene glycol phase while the cells and other fermentation products are concentrated in the lower dextran phase. This is described in Enzyme and Microb. Technol. Vol. 7, 333–338 (1985). The partition coefficient for alpha-amylase in that system had a maximum of 4, for example.

A variation of the above procedure is described in U.S. Pat. No. 4,508,825 wherein the extracellular enzyme-containing supernatant is separated from the cells, and the cell-free supernatant is mixed with polyethylene glycol and a cationic epihalohydrin/polyamine copolymer or dextran polymer to form two phases. This technique can be used to separate extracellular protease and amylase wherein the protease is concentrated in the polyethylene glycol phase and the amylase is concentrated in the cationic copolymer or dextran phase.

Two-phase enzyme recovery procedures have also been used with intracellular enzymes. U.S. Pat. No. 4,144,130 describes the use of (1) a mixture of a high molecular weight unsubstituted or substituted polyalcohol, polyether, polyester, polyvinylpyrrolidone or polysaccharide and an inorganic salt, or (2) a mixture of at least two of the above high molecular weight polymers to recover intracellular enzymes from an aqueous solution into which they have been released from the cells. When a mixture of polyethylene glycol and an inorganic salt, for example, is used, the desired intracellular enzyme goes into the top polyethylene glycol layer while the cell debris and other fermentation products go into the lower salt-containing layer. The partition coefficient for various enzymes recovered in the glycol layer was about 0.3 when a normal cell mass was treated. The partition coefficient was increased to only about 3 when frozen cells were mixed with water and disintegrated to release their enzymes.

The addition of polyethylene glycol to assist inorganic salts in the precipitation of enzymes from cell-free supernatant is disclosed in U.S. Pat. No. 4,016,039.

There has been no suggestion in the prior art that polyethylene glycol and inorganic salts could be used in a two-phase process to recover extracellular enzymes from whole fermentation beer with partition coefficients of at least 50.

SUMMARY OF THE INVENTION

In accordance with the present invention, a process for the recovery of an extracellular enzyme from whole fermentation beer is provided which comprises adding to whole fermentation beer containing microorganism cells and an extracellular enzyme a mixture of (a) a polymer selected from the class consisting of polyethylene glycol, an amine derivative of polyethylene glycol, a carboxylate derivative of polyethylene glycol, polypropylene glycol, an amine derivative of polypropylene glycol, a carboxylate derivative of polypropylene glycol, poly (ethylene glycol) ester, polyethyleneimine, trimethylamino-polyethylene glycol, polyvinyl alcohol, polyvinylpyrrolidone and mixtures thereof, and (b) an inorganic salt, allowing the whole fermentation beer-polymer-salt mixture to separate into an enzyme-rich polymer phase and an enzyme-poor salt phase, and recovering an enzymerich product therefrom.

DESCRIPTION OF THE INVENTION

The whole fermentation beers containing extracellular enzymes useful as raw material for the process of the present invention are well known in the art. *Bacillus licheniformis, Bacillus amyloliquefaciens, Bacillus subtilis* and *Mucor miehei*, for example, are known to produce extracellular enzymes, such as protease, amylase and microbial rennet, when grown in suitable nutrient media. The resulting mixture of cell debris, extracellular soluble enzymes and other fermentation products can be employed in the process of the present invention without any further separation of the cell debris from the soluble enzymes. As used herein, the term "cell debris" will mean whole cells as well as cell fragments.

The whole fermentation beer is then mixed with a polymer and an inorganic salt to form a two-phase system. The desired extracellular enzyme will collect in the polymer phase while the cell debris will collect in the salt phase.

Suitable polymers include polyethylene glycol, an amine derivative of polyethylene glycol, a carboxylate derivative of polyethylene glycol, polypropylene glycol, an amine derivative of polypropylene glycol, a carboxylate derivative of polypropylene glycol, poly (ethylene glycol) ester, polyethyleneimine, trimethylamino-polyethylene glycol, polyvinyl alcohol, polyvinylpyrrolidone and mixtures thereof. The preferred polymer is polyethylene glycol. Any form of polyethylene glycol which is soluble in the aqueous whole fermentation beer is suitable. An especially useful polyethylene glycol has a molecular weight of about 3350. It is solid at ambient temperature and can be conveniently handled on a commercial production scale.

The inorganic salt can be the compounds wherein the cations are sodium, potassium, magnesium and ammonium, and the anions are sulfates, carbonates, citrates, chlorides, phosphates and mixtures thereof. Preferred salts are sodium chloride and sodium sulfate.

The polymer and inorganic salt are added to the whole fermentation beer in amounts to form a total mixture which contains 64–90 percent whole fermentation beer, 1–15 percent polymer and 8–35 percent inorganic salt, said percentages being by weight based on the total weight of the mixture. It is preferred that the total mixture contain 73–79 percent whole fermentation beer, 3–4 percent polymer and 15–24 percent inorganic salt.

After addition of the polymer and salt, two phases will form. The polymer phase will usually be on top of the salt phase. The two phases can form by settling wherein the mixture is allowed to stand quietly for about 5 hours. The enzyme-containing polymer phase can then be separated by any standard liquid/liquid separatory technique, such as siphoning and decanting, to recover the enzyme. It is preferred, however, to use centrifugation to separate the phases. A useful separator is a continuous, solid-bowl centrifuge. In order to achieve a desirable concentration of enzyme in the final separated polymer phase, it is preferred that the volume ratio of the enzyme-rich polymer phase to the enzyme-poor salt phase be 0.12–0.15.

To most effectively recover the extracellular enzyme, the centrifuge should be operated so that none of the polymer phase is entrained with the salt phase which is to be discarded. The resulting collected polymer phase may have some entrained salt phase mixed therein. The mixture is then subjected to a secondary centrifuge separation wherein the centrifuge is operated so that none of the polymer phase is entrained with the salt phase and only a minor amount of salt phase is entrained with the polymer phase.

The enzyme-rich polymer phase so collected can be used directly as an enzyme source. An alkaline protease recovered in a polyethylene glycol phase for example, is suitable in enzyme detergent formulations. The glycol is useful as a stabilizer for the enzyme. If desired, the enzyme can be separated from the polymer by well-known techniques, such as precipitation, ultrafiltration or evaporation, to produce a substantially polymerfree enzyme product.

In a further preferred embodiment of the present invention, the whole fermentation beer is pretreated with a mixture of 1.5–5.0 percent calcium chloride dihydrate, 0.1–1.2 percent monosodium or monopotassium phosphate and 0–0.6 percent calcium hydroxide, said percentages being on weight/volume basis calculated on the weight of additive to volume of fermentation beer. This pretreatment step helps to flocculate the cell debris and improves the separation of enzyme from cell debris when the polymer and inorganic salt are subsequently added. Preferably, when a protease is being recovered, the pretreatment step should employ 1.5–5.0 percent calcium chloride dihydrate and 0.2–1.2 percent monosodium or monopotassium phosphate. When an amylase is being recovered, the pretreatment step should employ 1.5–5.0 percent calcium chloride dihydrate, 0.1–1.0 percent monosodium or monopotassium phosphate and 0.1–0.6 percent calcium hydroxide.

The partition coefficient is known in the art as a measure of effectiveness of separation. It is expressed as the enzyme activity concentration in the top or polymer phase divided by the enzyme activity concentration in the bottom or inorganic salt phase. The enzyme activity in each phase can be measured by well-known techniques. The process of the present invention can achieve partition coefficients of at least 50 which represents a significant advance over the known prior art.

The invention will be described in further detail in the following examples.

EXAMPLE 1

A nutrient medium suitable for production of alkaline protease was prepared by adding the following ingredients to a 6000 gallon (22712 l.) fermentor:
Wheat Gluten: 1500 lb (681 kg)
Sodium Citrate: 165 lb (74.9 kg)
Calcium Chloride Dihydrate: 165 lb (74.9 kg)
Corn Starch: 5000 lb (2270 kg)
Soy Meal: 2500 lb (1135 kg)
Heat-Stable Alpha Amylase: 5 lb (2.27 kg)
Monosodium Phosphate: 400 lb (181.6 kg)
Disodium Phosphate: 400 lb (181.6 kg)
Antifoam Agent: 16.5 gal (62.5 l)
Water to: 6000 gal (22712 l)

The medium was then inoculated with viable cells of *Bacillus licheniformis* and allowed to ferment for 36 hours at 36° C. To the resulting whole fermentation beer were added 214 gal (811 l) of 70 percent (w/v) aqueous calcium chloride dihydrate solution and 300 lb (136 kg) of monosodium phosphate. This results in a mixture containing 2.5 percent (w/v) calcium chloride dihydrate and 0.6 percent (w/v) monosodium phosphate based on the weight of each additive and the volume of the fermentation beer. The pH of the mixture was maintained at 6.8–7.6 while mixing in the additives by addition of sodium hydroxide. After mixing was complete, the pH was adjusted to 7.4–7.6 by addition of sodium hydroxide to complete the flocculation. The pH was then adjusted to 6.4–6.6 by addition of 50 weight percent aqueous acetic acid solution. To the resulting mixture were added 11600 lb (5260 kg) sodium chloride at 25°–27° C. and the mixture was stirred for 1 hr. to dissolve all the sodium chloride. Then 3100 lb (1400 kg) of polyethylene glycol having molecular weight of 3350 and 4250 lb (1930 kg) of sodium sulfate were added, and the whole beer temperature was increased to 30°–32° C. The pH of whole beer was adjusted to 6.0–6.2 by addition of acetic acid solution and the total mixture was stirred for 2 hr. The total mixture contained 15 percent (w/w) sodium chloride, 4 percent (w/w) polyethylene glycol, 5.5 percent (w/w) sodium sulfate and 75.5 percent (w/w) whole fermentation beer. The percentages were calculated on the weight of additive to total mixture weight of fermentation beer and additives. After mixing, the total mixture separated into an upper polyethylene glycol phase and a lower sodium chloride-sodium sulfate-cell debris phase. The phase ratio of upper phase volume to lower phase volume was 0.15. The concentration of protease activity in the upper phase divided by the concentration of protease activity in the lower phase resulted in a partition coefficient of 60–80. A continuous, solid-bowl centrifuge was then employed to separate the two phases. The centrifuge was adjusted for a primary separation wherein there was no polyethylene glycol phase entrainment in the salt phase which was discarded. The glycol phase contained 90–92 percent of the total enzyme activity of the fermentation beer. This glycol phase also contained about 5–20 volume percent salt phase entrainment. The glycol phase collected as above was then subjected to a secondary separation using similar equipment wherein the operating parameters were set so as to allow less than 2 volume percent entrainment of salt phase in the glycol phase. The salt phase was discarded, and it contained none of the glycol phase. The glycol phase collected as above was then placed in a chilled tank at 10° C. to remove trace amounts of sodium sulfate. A small quantity of sodium sulfate crystals were added to induce growth of sodium sulfate crystals. After 2 hours with mild agitation at 10° C., the sodium sulfate-free glycol phase was drained off. It was then mixed with activated carbon and filter aid and then filtered using a filter press. The resulting alkaline protease-rich glycol solution can be used directly in liquid enzyme detergent formulations.

EXAMPLE 2

The procedure of Example 1 was repeated through the step of adding the calcium chloride dihydrate and monosodium phosphate. The resulting whole fermentation beer-additive mixture was then mixed with 2130 lb (970 kg) polyethylene glycol having molecular weight of 3350 and 10660 lb (4850 kg) sodium sulfate, and the whole beer temperature was raised to 30°–32° C. The total mixture containing 3 percent (w/w) polyethylene glycol, 15 percent (w/w) sodium sulfate and 82 percent (w/w) whole fermentation beer was then stirred for 1 hour. After mixing, the total mixture separated into an upper polyethylene glycol phase and a lower sodium sulfate-cell debris phase. The phase ratio of upper phase volume to lower phase volume was 0.12. The concentration of protease activity in the upper phase divided by the concentration of protease activity in the lower phase resulted in a partition coefficient of 60–80. The alkaline protease in the glycol phase was in the form of an amorphous solid. The two phases were then separated by a centrifuge as described in Example 1 to produce a glycol phase containing amorphous solid protease and less than 2 volume percent entrainment of the salt phase. The solids were then recovered by centrifugation, and they can be used as granular protease in granular enzyme detergent products.

EXAMPLE 3

A nutrient medium suitable for production of heat-stable alpha-amylase was prepared by adding the following ingredients to a 6000 gallon (22712 l.) fermentor:
Calcium Chloride Dihydrate: 22.5 lb (10.2 kg)
Monopotassium Phosphate: 300 lb (136.2 kg)
Dipotassium Phosphate: 700 lb (317.8 kg)
Ammonium Sulfate 250 lb (113.5 kg)
Sodium Citrate: 100 lb (45.4 kg)
Corn Steep Liquor: 1000 lb (454 kg)
Lactose: 7000 lb (3178 kg)
Cotton Seed Meal: 1500 lb (681 kg)
Soy Meal: 2000 lb (908 kg)
Antifoam Agent: 165 gal (625 l)
Water to: 6000 gal (22712 l)
The medium was then inoculated with viable cells of Bacillus licheniformis and allowed to ferment for 108–110 hours at 42° C. while maintaining the pH at 7.05–7.15 by periodic addition of sodium hydroxide. To the resulting whole fermentation beer were added 343 gal (1300 l) of 70 percent (w/v) aqueous calcium chloride dihydrate solution, 240 gal (908 l) of 10 percent (w/v) aqueous calcium hydroxide solution and 60 lb (27 kg) monopotassium phosphate. This results in a mixture containing 4 percent (w/v) calcium chloride dihydrate, 0.4 percent (w/v) calcium hydroxide and 0.12 percent (w/v) monopotassium phosphate based on the weight of each additive and the volume of the fermentation beer. The pH of the mixture was maintained at 7.6–8.4 while mixing in the additives by addition of sodium hydroxide. After mixing was complete, the pH was adjusted to 8.4–8.6 by addition of sodium hydroxide. To the resulting mixture were added 2600 lb (1180 kg) of polyethylene glycol having molecular weight of 3350 and 7420 lb (3370 kg) sodium chloride at 25°–27° C., and the mixture was allowed to agitate for at least 1 hour. Sodium sulfate in an amount of 5940 lb (2700 kg) was then added, and the fermentation beer mixture was heated to 30°–32° C. The pH was adjusted to 7.9–8.1 by addition of sodium hydroxide, and the total mixture was stirred for at least 2 hours. The total mixture contained 3.5 percent (w/w) polyethylene glycol, 10 percent (w/w) sodium chloride, 8 percent (w/w) sodium sulfate and 78.5 percent (w/w) whole fermentation beer. After mixing, the total mixture separated into an upper polyethylene glycol phase and a lower sodium chloride-sodium sulfate-cell debris phase. The phase ratio of upper phase volume to lower phase volume was 0.12. The concentration of amylase activity in the upper phase divided by the concentration of amylase activity in the lower phase resulted in a partition coefficient of 50–70. A continuous, solid-bowl centrifuge was employed as described in Example 1 to recover an amylase-rich glycol phase which was then purified as described in Example 1 to produce an amylase-rich glycol product.

EXAMPLE 4

A nutrient medium suitable for production of alpha-amylase was prepared by adding the following ingredients to a 6000 gallon (22712 l) fermentor:
Calcium Carbonate: 530 lb (240.6 kg)
Fish Meal: 750 lb (340.5 kg)
Ground Soy Meal: 2800 lb (1271 kg)
Corn Steep Liquor: 1500 lb (681 kg)
Lactose: 7000 lb (3178 kg)
Diammonium Phosphate: 130 lb (59 kg)
Antifoam Agent: 40 gal (151.4 l)
Water to: 6000 gal (22712 l)
The medium was then inoculated with viable cells of Bacillus amyloliquefaciens and allowed to ferment for 60 hours at 34° C. while maintaining the pH at 7.05–7.15 by periodic addition of sodium hydroxide. To the resulting whole fermentation beer were added 257 gal (973 l) of 70 percent (w/v) aqueous calcium chloride dihydrate solution, 180 gal (681 l) of 10 percent (w/v) aqueous calcium hydroxide solution and 300 lb (136 kg) monopotassium phosphate. This results in a mixture containing 3 percent (w/v) calcium chloride dihydrate, 0.3 percent (w/v) calcium hydroxide and 0.6 percent (w/v) monopotassium phosphate based on the weight of each additive and the volume of the fermentation beer. The pH of the mixture was maintained at 6.8–7.6 while mixing in the additives by addition of sodium hydroxide. After mixing was complete, the pH was adjusted to 7.4–7.6 by addition of sodium hydroxide. To the resulting mixture were added 2510 lb (1140 kg) of polyethylene glycol having molecular weight of 3350 and 7960 lb (3600 kg) sodium chloride at 25°–27° C., and the mixture was allowed to agitate for at least 1 hour. Sodium sulfate in an amount of 10700 lb (4870 kg) was then added, and the fermentation beer mixture was heated to 30°–32° C. The pH was adjusted to 7.4–7.6 by addition of sodium hydroxide, and the total mixture was stirred for at least 2 hours. The total mixture contained 3.15 percent (w/w) polyethylene glycol, 10 percent (w/w) sodium chloride, 13.5 percent (w/w) sodium sulfate and 73.35 percent (w/w) whole fermentation beer. After mixing, the total mixture separated into two phases as described in Example 3 having a phase ratio of 0.12 and a partition coefficient of 50–70. The phases were treated as described therein to produce an amylase-rich glycol product.

What is claimed is:

1. A process for the recovery of an extracellular enzyme from whole fermentation beer which comprises adding to whole fermentation beer containing microorganism cells and an extracellular enzyme a mixture of (a) a polymer selected from the class consisting of polyethylene glycol, an amine derivative of polyethylene glycol, a carboxylate derivative of polyethylene glycol, polypropylene glycol, an amine derivative of polypropylene glycol, a carboxylate derivative of polypropylene glycol, poly (ethylene glycol) ester, polyethyleneimine, trimethylamino-polyethylene glycol, polyvinyl alcohol, polyvinylpyrrolidone and mixtures thereof, and (b) an inorganic salt, allowing the whole fermentation beer-polymer-salt mixture to separate into an enzyme-rich polymer phase and an enzyme-poor salt phase, and recovering an enzyme-rich product therefrom.

2. A process of claim 1 wherein the inorganic salt is selected from the class of compounds wherein the cations are sodium, potassium, magnesium and ammonium and the anions are sulfates, carbonates, citrates, chlorides, phosphates and mixtures thereof.

3. A process of claim 1 wherein the total mixture of whole fermentation beer, polymer and inorganic salt contains 64–90 percent whole fermentation beer, 1–15 percent polymer and 8–35 percent inorganic salt, said percentages are by weight based on the total weight of the mixture.

4. A process of claim 1 wherein the total mixture of whole fermentation beer, polymer and inorganic salt contains 73–79 percent whole fermentation beer, 3–4 percent polymer and 15–24 percent inorganic salt, said percentages are by weight based on the total weight of the mixture.

5. A process of claim 4 wherein the polymer is polyethylene glycol and the inorganic salt is a mixture of sodium chloride and sodium sulfate.

6. A process of claim 4 wherein the polymer is polyethylene glycol and the salt is sodium sulfate.

7. A process of claim 4 wherein the polymer is polyethylene glycol having a molecular weight of about 3350.

8. A process of claim 4 wherein prior to adding the polymer and inorganic salt mixture, the whole fermentation beer is contacted with a mixture of 1.5–5.0 percent calcium chloride dihydrate, 0.1–1.2 percent monosodium or monopotassium phosphate and 0–0.6 percent calcium hydroxide, said percentages being on weight/volume basis calculated on the weight of additive to volume of fermentation beer.

9. A process of claim 8 wherein the whole fermentation beer is contacted with a mixture of 1.5–5.0 percent calcium chloride dihydrate and 0.2–1.2 percent monosodium phosphate or monopotassium phosphate.

10. A process of claim 8 wherein the whole fermentation beer is contacted with a mixture of 1.5–5.0 percent calcium chloride dihydrate, 0.1–0.6 percent calcium hydroxide and 0.1–1.0 percent monosodium or monopotassium phosphate.

11. A process of claim 4 wherein the volume ratio of the enzyme-rich polymer phase to the enzyme-poor salt phase is 0.12–0.15.

12. A process of claim 4 wherein the resulting phases are separated by a continuous, solid-bowl centrifuge.

13. A process for the recovery of an extracellular alkaline protease which comprises fermenting a suitable strain of *Bacillus licheniformis* in an appropriate nutrient medium to produce a whole fermentation beer containing *Bacillus licheniformis* cells and extracellular alkaline protease, adding to said whole fermentation beer 2.5 percent calcium chloride dihydrate and 0.6 percent monosodium or monopotassium phosphate, said percentages being on a weight/volume basis calculated on the weight of additive to volume of fermentation beer, adding to the above mixture 3 percent polyethylene glycol and 15 percent sodium sulfate, said percentages being by weight based on the total mixture weight of fermentation beer and additives, forming an alkaline protease-rich polyethylene glycol phase and an alkaline protease-poor sodium sulfate phase, and separating the two phases to recover an alkaline protease-rich product therefrom.

14. A process of claim 13 wherein after adding the calcium chloride dihydrate and monosodium or monopotassium phosphate, the mixture is contacted with 15 percent sodium chloride, 4 percent polyethylene glycol and 5.5 percent sodium sulfate, said percentages being by weight based on the total mixture weight of fermentation beer and additives.

15. A process for the recovery of an extracellular heat-stable alpha-amylase which comprises fermenting a suitable strain of *Bacillus licheniformis* in an appropriate nutrient medium to produce a whole fermentation beer containing *Bacillus licheniformis* cells and extracellular alpha-amylase, adding to said whole fermentation beer 0.4 percent calcium hydroxide, 0.12 percent monosodium or monopotassium phosphate and 4 percent calcium chloride dihydrate, said percentages being on a weight/volume basis calculated on the weight of additive to volume of fermentation beer, adding to the above mixture 3.5 percent polyethylene glycol, 10 percent sodium chloride and 8 percent sodium sulfate, said percentages being by weight based on the total mixture weight of fermentation beer and additives, forming an amylase-rich polyethylene glycol phase and an amylase-poor sodium chloride-sodium sulfate phase and separating the two phases to recover an amylase-rich product therefrom.

16. A process for the recovery of an extracellular alpha-amylase which comprises fermenting a suitable strain of *Bacillus amyloliquefaciens* in an appropriate nutrient medium to produce a whole fermentation beer containing *Bacillus amyloliquefaciens* cells and extracellular alpha-amylase, adding to said whole fermentation beer 3 percent calcium chloride dihydrate, 0.3 percent calcium hydroxide and 0.6 percent monosodium or monopotassium phosphate, said percentages being on a weight/volume basis calculated on the weight of additive to volume of fermentation beer, adding to the above mixture 3.15 percent polyethylene glycol, 10 percent sodium chloride and 13.5 percent sodium sulfate, said percentages being by weight based on the total mixture weight of fermentation beer and additives, forming an amylase-rich polyethylene glycol phase and an amylase-poor sodium chloride-sodium sulfate phase and separating the two phases to produce an amylase-rich product therefrom.

* * * * *